(12) United States Patent
Soroudi

(10) Patent No.: US 7,513,893 B2
(45) Date of Patent: Apr. 7, 2009

(54) DEVICE AND METHOD FOR TREATMENT OF EYELID DISEASES

(76) Inventor: Abraham Ebbie Soroudi, 11740 W. Sunset Blvd., Brentwood, CA (US) 90049

( * ) Notice: Subject to any disclaimer, the term of this patent is extended or adjusted under 35 U.S.C. 154(b) by 121 days.

(21) Appl. No.: 11/324,848

(22) Filed: Jan. 3, 2006

(65) Prior Publication Data

US 2006/0104914 A1    May 18, 2006

Related U.S. Application Data

(63) Continuation-in-part of application No. 10/799,209, filed on Mar. 12, 2004, now Pat. No. 7,211,070.

(51) Int. Cl.
*A61M 35/00* (2006.01)
(52) U.S. Cl. ............... 604/294; 604/289
(58) Field of Classification Search ......... 604/289–291, 604/294–296; 607/109
See application file for complete search history.

(56) References Cited

U.S. PATENT DOCUMENTS

| | | | |
|---|---|---|---|
| 2,527,947 A * | 10/1950 | Loos | ............ 604/294 |
| 2,573,791 A | 11/1951 | Howells | |
| 2,765,789 A | 10/1956 | Schmierer | |
| 3,762,419 A * | 10/1973 | Walters | ............ 607/109 |
| 3,804,077 A * | 4/1974 | Williams | ............ 126/263.1 |
| 4,134,401 A | 1/1979 | Galician | |
| 4,268,272 A | 5/1981 | Taura | |
| 4,372,318 A | 2/1983 | Viesturs et al. | |
| 4,516,564 A | 5/1985 | Koiso et al. | |
| 4,666,441 A | 5/1987 | Andriola et al. | |
| 4,995,114 A | 2/1991 | Price, Jr. | |
| 5,389,066 A | 2/1995 | Rhame, Jr. | |
| 5,456,704 A | 10/1995 | Kilcullen | |
| 5,769,806 A | 6/1998 | Radow | |
| 5,879,378 A | 3/1999 | Usui | |
| 6,090,060 A | 7/2000 | Radow | |
| 6,149,615 A | 11/2000 | Gallamore | |
| 6,261,595 B1 | 7/2001 | Stanley et al. | |
| 6,409,746 B1 | 6/2002 | Igaki et al. | |
| 6,436,128 B1 | 8/2002 | Usui | |
| 6,623,517 B1 | 9/2003 | DeLuisa et al. | |
| 6,629,964 B1 | 10/2003 | Ono et al. | |
| 2003/0056281 A1 | 3/2003 | Hasegawa | |
| 2004/0074502 A1 | 4/2004 | Abbasi | |
| 2006/0018953 A1 * | 1/2006 | Guillon et al. | ............ 424/443 |

FOREIGN PATENT DOCUMENTS

WO        93/10019    *  5/1993

* cited by examiner

*Primary Examiner*—Michele Kidwell
(74) *Attorney, Agent, or Firm*—Blakely, Sokoloff, Taylor & Zafman LLP

(57) ABSTRACT

A container has an impermeable outer membrane sized to fit generally within the peri-orbital region and sufficiently flexible to mold to the structure of the closed eye. Heat which is generated by an exothermic reaction inside the container, which provides steady-state heat to the eyelids. A soft, non-abrasive, lint-free material is presoaked in a pH controlled (preferably antibacterial and hypoallergenic) detergent, with or without an ophthalmic antibiotic solution. The compress may also have a handle which makes holding and maneuvering the compress more feasible, while protecting the user's fingers from the heat, and preventing the contamination of the compress by the fingers. The compress may be packed in a watertight, sterile wrapper which will prevent drying of the detergent solution. Other embodiments are also described and claimed.

23 Claims, 17 Drawing Sheets

DEVICE AND METHOD FOR TREATMENT OF EYELID DISEASES

This continuation-in-part application claims the benefit of the earlier filing date of U.S. patent application Ser. No. 10/799,209, filed Mar. 12, 2004, entitled "Device and Method for Exothermic Treatment of Eyelid Diseases" now U.S. Pat. No. 7,211,070.

BACKGROUND

There is a myriad of common eye disease known in the field of Ophthalmology that benefit from the use of warm compresses applied to the periocular skin. A combination of heat application and scrubbing the eyelids with a mild detergent (e.g., a pH-controlled "baby" shampoo) is the currently accepted means of achieving proper eyelid hygiene, and is the common denominator in the treatment of a variety of very common eye conditions.

Acutely inflamed internal or external hordeola or chalazia (Collectively referred to as Sties) are probably the most widely recognized and accepted indications for using warm compresses on the eyes. These conditions are extremely common, they're recurrent, and occur in children and adults alike, with equal distribution in males and females. Sties are small "lumps" that can form over or under the eyelids, or on the bases of the eyelashes. They typically result from the clogging of oil (sebaceous) or sweat glands around the eyelashes or inside the eyelid, and are thought to be brought about by bacterial overgrowth. They can cause tremendous redness, tenderness, pain, tearing and even light-sensitivity, followed by progressive swelling in a small area or the entire eyelid.

Patients often use a warm tea-bag or a towelette that they hold under warm running water, both of which lose heat within mere seconds. Some run their eyes under hot tap water or try microwave-heated compresses with resulting second-degree burns severe enough to have even been reported in the scientific literature. Some specialists advocate the use of a boiled egg or a warm potato wrapped in a thin towel (burrito) to provide heat for a longer duration of time. These methods of applying heat are often either not hot enough or not lengthy enough to be effective, and on the same token, can be hot enough to be harmful to the delicate periocular skin.

The application of heat and pH-controlled detergent (e.g., "baby shampoo") scrubs has also been advocated toward the treatment of many other ocular conditions such as blepharitis (staphylococcal vs. seborrheic), meibomian gland dysfunction, preseptal/orbital cellulitis, and dry eye syndrome.

In the case of blepharitis, the addition of a mild, broad-spectrum antibiotic (e.g., erythromycin or bacitracin), even steroids (e.g., prednisolone acetate 1% ophthalmic solution) may be supplemented with the warm pH-controlled shampoo scrubs per the discretion of the ophthalmologist.

Blepharitis refers to chronic inflammation of the eyelids, and is one of the most common disorder of the eye. Blepharitis may be anterior, e.g. staphycoccal, seborrheic or posterior, e.g. meibomian gland dysfunction.

Blepharitis is often the underlying reason for eye discomfort, redness and tearing, burning, itching, light sensitivity, and an irritating, sandy, gritty sensation that is worse upon awakening.

Warm compresses followed by lid scrubs is an element of effective blepharitis control. Many ophthalmologists recommend cotton-tip applicators be used to scrub the eyelids and lashes with a pH-controlled shampoo, before or after the application of moist heat. Not only is this exercise tedious and inconvenient for even young, healthy individuals, but is quite a difficult task for children or for the elderly, especially those who suffer from arthritis, those who fatigue easily, have poor near visual acuity, or those whose hands shake. The inconvenience of this ritual is a common cause of poor compliance and treatment failure frequently encountered in clinical practice.

The recommended step-by-step treatment for sties and blepharitis is to:
1) cleanse the oily eyelid margin with a non-toxic (preferably antibacterial) detergent,
2) massage the eyelids to help "unclog" the pores, and
3) provide enough heat to:
    i) help open the clogged pores,
    ii) emulsify the lipogranulomatous component of the meibomian contents (like melting butter to turn it into fluid), which would aid drainage and absorption, and
    iii) improve blood flow to the affected site to expedite absorption.

Acute hordeola, if not treated properly initially, can turn into chalazia, which are hard, painless eyelid masses, and require intralesional steroid injections, even surgical debridement, both of which could be easily prevented by proper and timely intervention.

On a different note, the bacterial flora residing on the eyelid margins has been known to be a source for devastating eye infections (endophthalmitis) following any type of ocular surgery, including LASIK, Corneal Transplantation, Cataract, Glaucoma, and Retinal surgery). In fact, in the face of poor eyelid hygiene or active blepharitis, it is contraindicated to perform any type of elective eye surgery. Today, pre-treatment of the eyelids with warm compresses and a pH-controlled shampoo has become a routine exercise for the thousands of people undergoing ocular surgery in the U.S. on a daily basis.

SUMMARY OF THE INVENTION

In one aspect of the present invention, the step-by-step ritual of frequent use of warm compresses and scrubbing the lids with a pH-controlled detergent (with or without the application of an antibiotic) is replaced with a much more convenient procedure which combines these steps into one.

In one embodiment, a product is provided that makes treating those affected by the aforementioned eye diseases (e.g., sties and blepharitis) more convenient and safe, thereby more effective.

In another aspect of the present invention, a convenient product promotes better eyelid hygiene by making this exercise less tedious, thereby improving patient compliance with the gold standard of treatment, while preventing the recurrence of the underlying problem (e.g., blepharitis or sties).

In yet another aspect, a convenient method for reducing the potential infectious complications of intraocular surgery is provided.

In another aspect, the invention provides pain relief to sufferers of certain conditions of the eye, such as dry eyes, or post-surgical pain.

DETAILED DESCRIPTION OF THE INVENTION

In a first aspect, the disclosure shows a warm compress or eye pad (hereafter referred to as "compress") that provides controlled heat energy generated by an exothermic reaction over a non-abrasive, lint-free material pre-soaked in a pH-controlled, cleansing detergent. The compress is provided to facilitate and make safe the simultaneous application of heat and scrubbing of the eyelid margins and the lashes with the detergent, with or without an ophthalmic antibiotic formulation.)

The eye pad is sufficiently flexible to conform to the shape of the closed eye, yet sufficiently stiff to be rolled over that area. As used herein, the term "impermeable" means that the contents of the container that is created by the impermeable membrane cannot pass through that membrane under ordinary use of the system. The term "permeable" means that the contents of adjoining compartments separated by the permeable membrane can mix with each other by passage through the permeable membrane.

In a particular embodiment, the separating membrane is rendered permeable by breakage of the membrane. The term "membrane" refers to a flexible or inflexible barrier.

Figure 1:
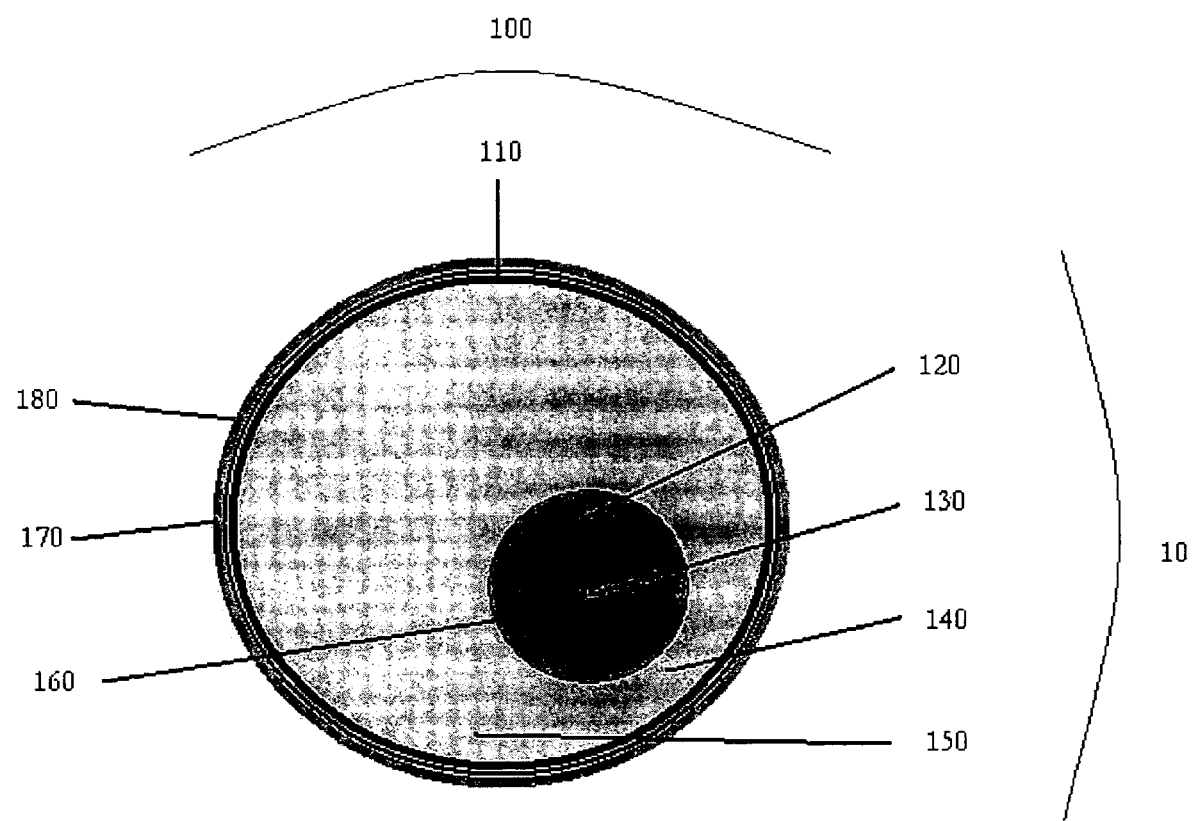
FIG. 1 shows a cross sectional view of an eye pack.

Referring now to FIG. 1 which shows eye pad system 10, multipart container 100 having impermeable outer membrane 110 is sized to fit generally within a user's peri-orbital region, and is sufficiently flexible to mold to that region of the user's face. First chemical 120 is stored in first, inner, concentric storage area 130 of multipart container 100. Second chemical 140 is stored in second, outer, concentric storage area 150 of multipart container 100. The first and second chemicals have been chosen to cause an exothermic reaction when mixed. Internal membrane 160 separates the first and second chemicals in container 100. Internal membrane 160 can be rendered permeable through such actions as the application of physical force to container 100, while at the same time impermeable outer membrane 110 maintains its impermeability.

Figure 7:
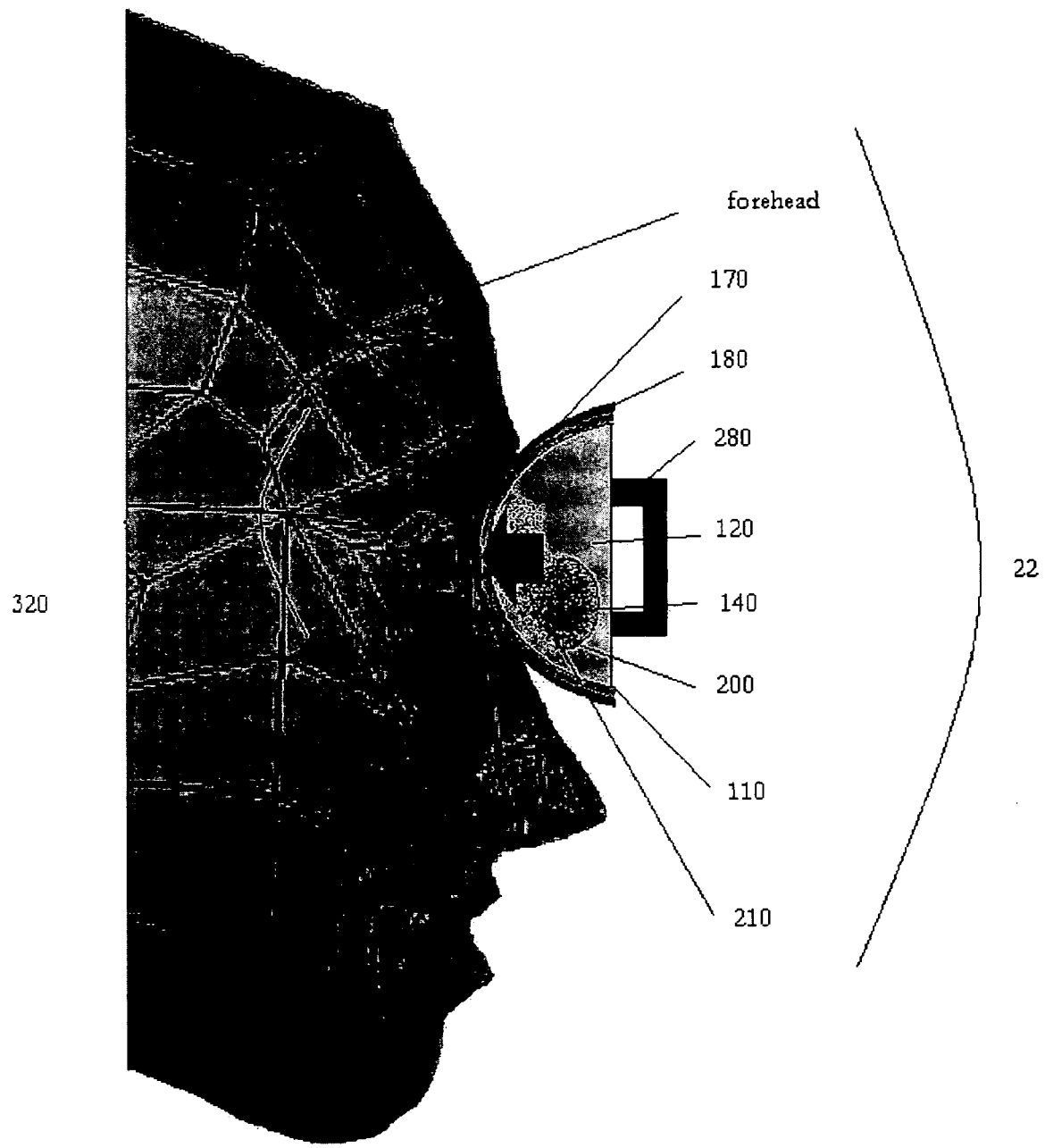
FIG. 7 shows an eye pad on the peri-orbital region.

Outer wrap 170 covers at least part of impermeable outer membrane 110 and is attached at enough places to create a soft surface at least the size of the peri-orbital region. Outer wrap 170 may completely cover multipart container 100 as shown, or it may cover a smaller part of container 100, such as only the portion of impermeable outer membrane 110 that would otherwise come in contact with the user's face, as shown in FIG. 7. Outer wrap 170 is preferably made of a soft, non-abrasive, lint-free material 180 such as gauze. Material 180 is suitable for absorbing and retaining a cleansing substance suitable for cleansing the peri-orbital region. Material 180 is also suitable for absorbing and retaining a topical non-allergenic bacteriostatic or bactericidal antibiotic. Material 180 is also flexible in the region to be applied to the face so that the contained cleanser and/or antibiotic can be moved around the peri-orbital region to cleanse the region.

Figure 2:
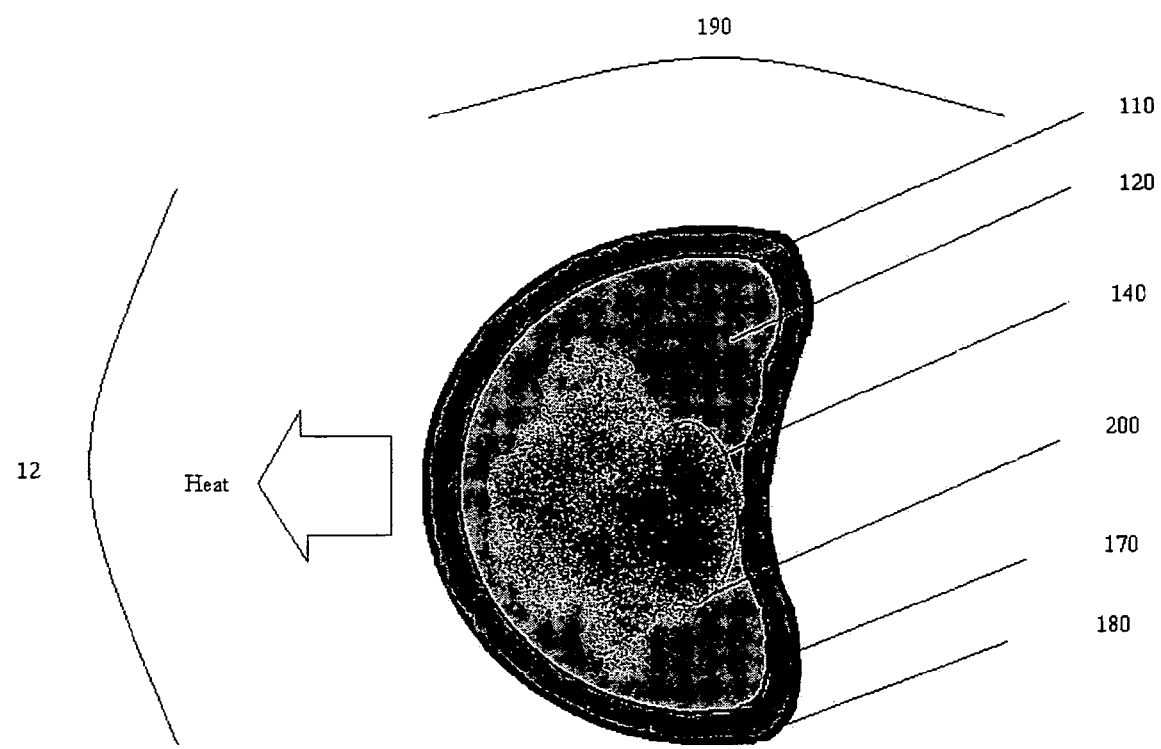
FIG. 2 shows the cross sectional view of the eye pack with burst inner membrane and resulting exothermic reaction.

Referring now to FIG. 2 and eye pad system 12, container 190 having impermeable outer membrane 110 is sized to fit generally within a user's peri-orbital region, and is sufficiently flexible to mold to the eye region of the user's face. Internal membrane 200 has been rendered permeable by rupture. First chemical 120 and second chemical 140 are mixed in container 190. The first and second chemicals have been chosen to cause an exothermic reaction when mixed, releasing heat from the system 12. Impermeable outer membrane 110 remains impermeable when internal membrane 200 is rendered permeable. Outer wrap 170, which covers at least the area to be placed on the user's face (see FIG. 7), is preferably made of soft, non-abrasive, lint-free material 180 such as gauze. Material 180 is suitable for absorbing and retaining a cleansing substance suitable for cleansing the peri-orbital region. Material 180 is also suitable for absorbing and retaining a topical non-allergenic bacteriostatic or bactericidal antibiotic. Material 180 is also flexible in the region to be applied to the face so that the contained cleanser and/or antibiotic can be moved around the peri-orbital region to cleanse the region.

Figure 3:
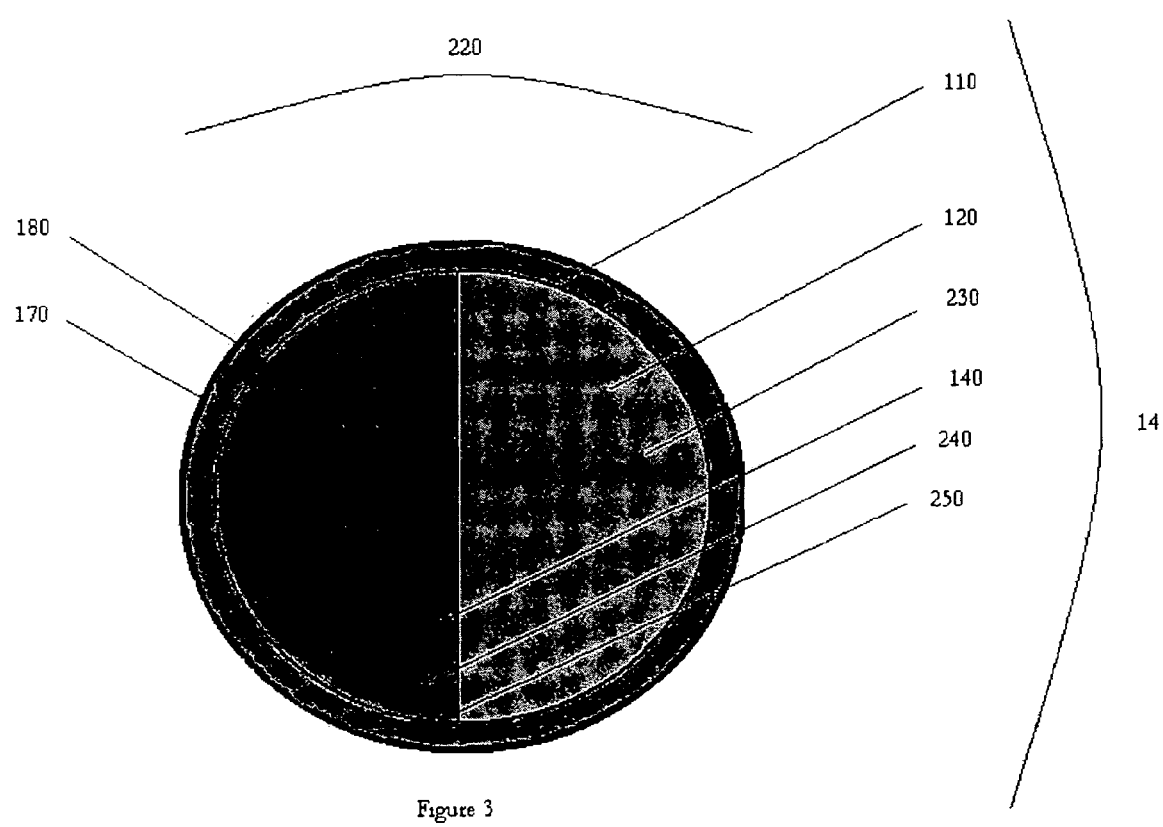
FIG. 3 shows an alternative cross sectional view of the exothermic heat pack.

FIG. 3 is similar to FIG. 1, showing an eye pad system 14 having multipart container 220 with impermeable outer membrane 110 that is sized to fit generally within a user's peri-orbital region, and is sufficiently flexible to mold to the eye region of the user's face. First chemical 120 is stored in first adjacent storage area 230 of multipart container 220. Second chemical 140 is stored in second adjacent storage area 240 of multipart container 220, abutting first adjacent storage area 230. The first and second chemicals have been chosen to cause an exothermic reaction when mixed. Internal membrane 250 that can be rendered permeable, separates the first and second chemicals in container 220. Internal membrane 250 can be rendered permeable through such actions as the application of physical force to container 220 while at the same time the impermeablity of outer membrane 110 is maintained. Outer wrap 170, which covers at least the area to be placed on the user's face (see FIG. 7), is made of soft, non-abrasive, lint-free material 180 such as gauze. Material 180 is suitable for absorbing and retaining a cleansing substance suitable for cleansing the peri-orbital region. Material 180 is also suitable for absorbing and retaining a topical non-allergenic bacteriostatic or bactericidal antibiotic. Material 180 is also flexible in the region to be applied to the face so that the contained cleanser and/or antibiotic can be moved around the peri-orbital region to cleanse the region.

Figure 4:
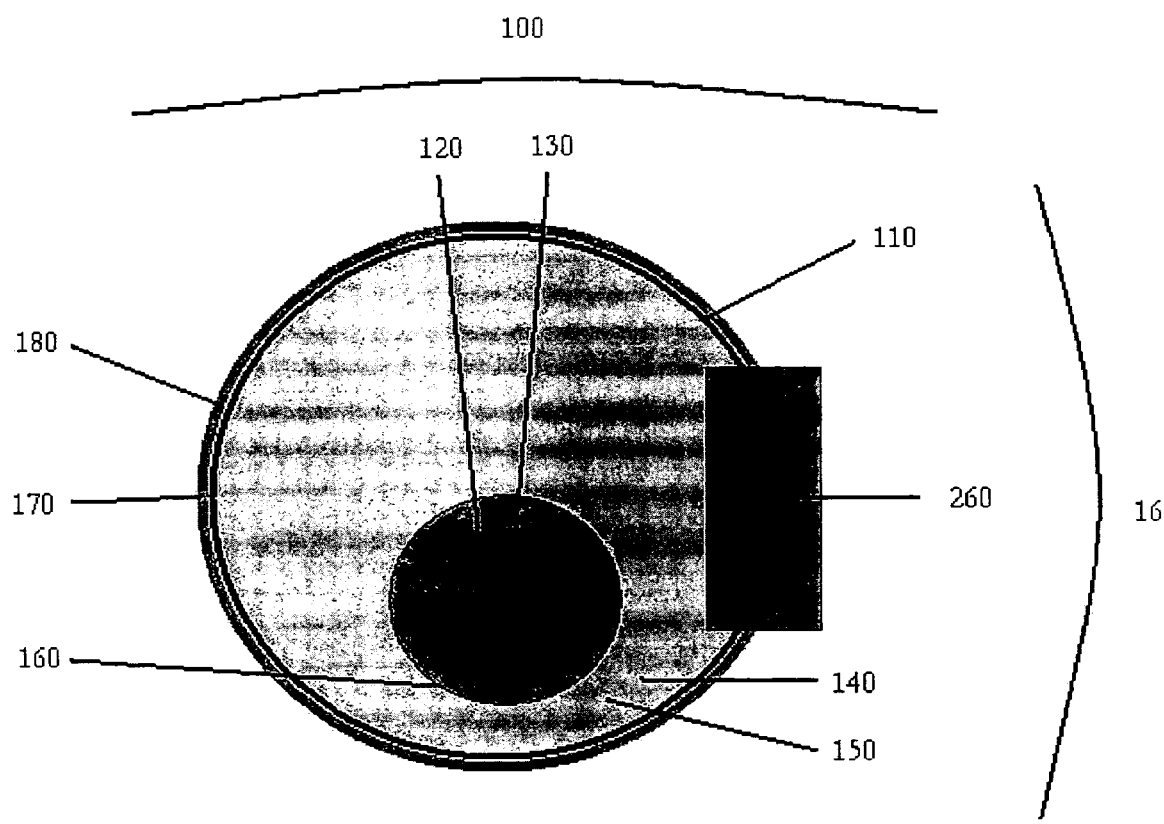
FIG. 4 shows a cross sectional view of an exothermic heat pack with an external handle.

Referring now to FIG. 4 and eye pad system 16, multipart container 100 having impermeable outer membrane 110 is sized to fit generally within a user's peri-orbital region, and is sufficiently flexible to mold to that region of the user's face. First chemical 120 is stored in first, inner, storage area 130 of multipart container 100. Second chemical 140 is stored in second, outer, storage area 150 of multipart container 100. The first and second chemicals have been chosen to cause an exothermic reaction when mixed. Internal membrane 160 separates the first and second chemicals in container 100. The area 130 defines a container that can move around inside the area 150. Internal membrane 160 can be rendered permeable through such actions as the application of physical force to container 100 while at the same time the impermeablity of outer membrane 110 is maintained.

Outer wrap 170 covers at least part of impermeable outer membrane 110 and is attached at enough places to create a smooth surface at least the size of the peri-orbital region. Outer wrap 170 may completely cover multipart container 100, or it may cover a smaller part of container 100, such as the portion of impermeable outer membrane 110 that would otherwise come in contact with the user's face, as shown in FIG. 7. Outer wrap 170 is made of soft, non-abrasive, lint-free material 180 such as gauze. Material 180 is suitable for absorbing and retaining a cleansing substance suitable for cleansing the peri-orbital region. Material 180 is also suitable for absorbing and retaining a topical non-allergenic bacteriostatic or bactericidal antibiotic. Material 180 is also flexible in the region to be applied to the face so that the contained cleanser and/or antibiotic can be moved around the peri-orbital region to cleanse the region.

External handle 260 can be rigidly attached to impermeable outer membrane 110 to provide a convenient way for a user to hold the eye pad. External handle 260 is also useful in the manual rupture of internal membrane 160 by providing a means for grasping and pushing firmly on outer membrane 110. Likewise, external handle 260 can be useful in the manipulation of system 16, especially around the peri-orbital region.

Figure 5:
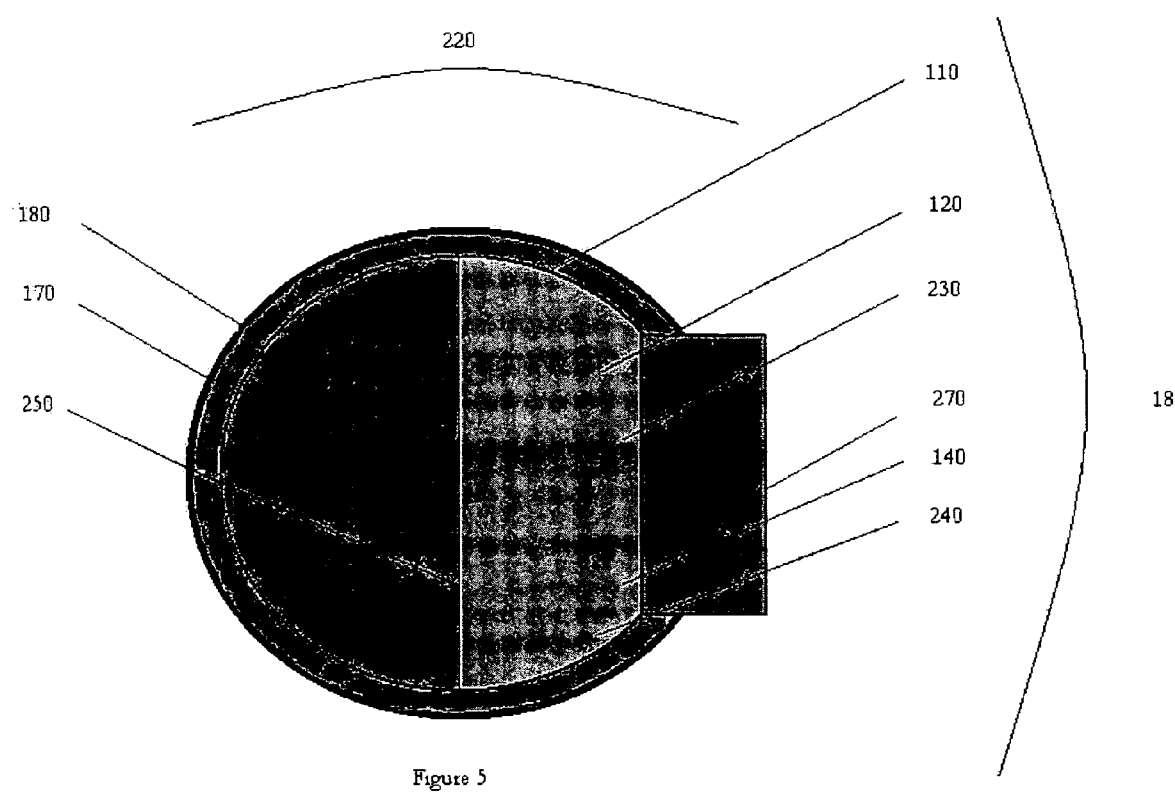
FIG. 5 shows a cross sectional view of an alternative exothermic heat pack with a penetrating handle.

Referring now to FIG. 5, and eye pad system 18, multipart container 220 with impermeable outer membrane 110, is sized to fit generally within a user's peri-orbital region, and is sufficiently flexible to mold to the eye region of the user's face. First chemical 120 is stored in first adjacent storage area 230 of multipart container 220. Second chemical 140 is stored in second adjacent storage area 240 of multipart container 220, abutting first adjacent storage area 230. The first and second chemicals have been chosen to cause an exothermic reaction when mixed. Interior membrane 250 that can be rendered permeable, separates the first and second chemicals in container 220. Internal membrane 250 can be rendered permeable through such actions as the application of physical force to container 220 while at the same time the impermeablity of outer membrane 110 is maintained. Outer wrap 170, which covers at least the area to be placed on the user's face (see FIG. 7), is made of soft, non-abrasive, lint-free material 180 such as gauze. Material 180 is suitable for absorbing and retaining a cleansing substance suitable for cleansing the peri-orbital region. Material 180 is also suitable for absorbing and retaining a topical non-allergenic bacteriostatic or bactericidal antibiotic. Material 180 is also flexible in the region to be applied to the face so that the contained cleanser and/or antibiotic can be moved around the peri-orbital region to cleanse the region.

Penetrating handle 270 can be rigidly attached to impermeable outer membrane 110 to provide a convenient way for a user to hold the eye pad. The presence of a portion of penetrating handle 270 inside first storage area 230 adds further stability to penetrating handle 270. Penetrating handle 270 is useful in the manual rupture of internal membrane 250 by providing a means for grasping and pushing firmly on outer membrane 110. Likewise, penetrating handle 270 can be useful in the manipulation of system 18, especially around the peri-orbital region.

Figure 6:
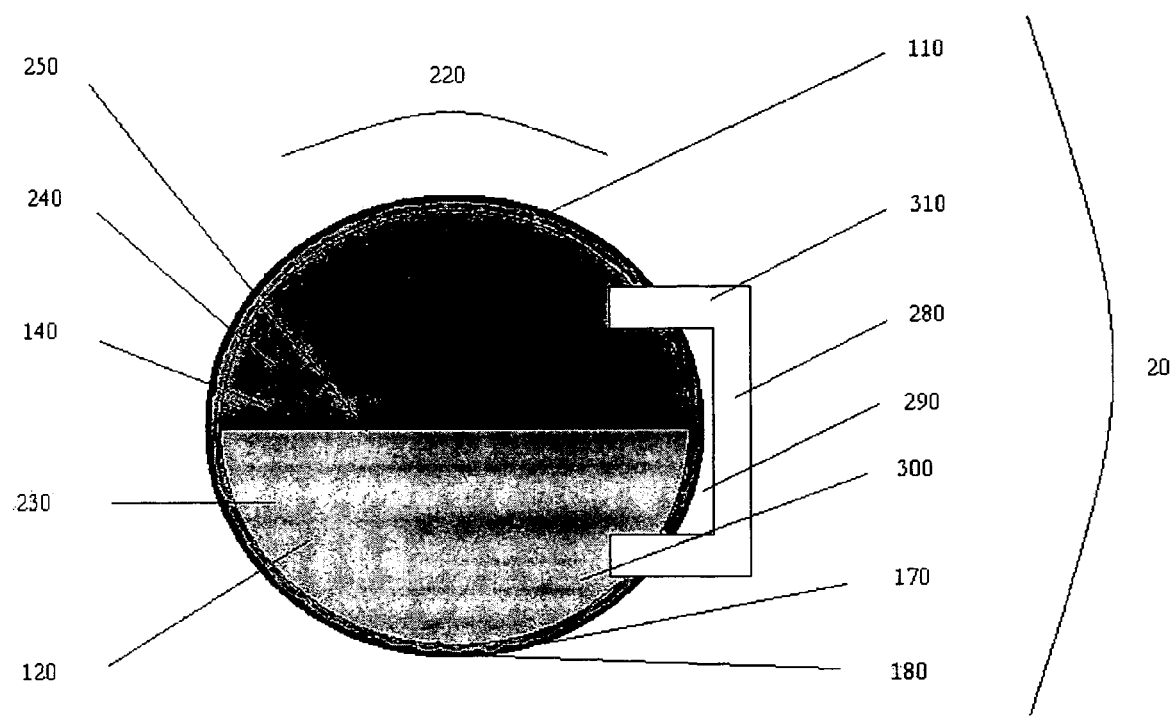
FIG. 6 shows a cross sectional view of an exothermic heat pack with an arcuate handle.

Referring now to FIG. 6, and eye pad system 20, multipart container 220 with impermeable outer membrane 110, is sized to fit generally within a user's peri-orbital region, and is sufficiently flexible to mold to the eye region of the user's face. First chemical 120 is stored in first adjacent storage area 230 of multipart container 220. Second chemical 140 is stored in second adjacent storage area 240 of multipart container 220, abutting first adjacent storage area 230. The first and second chemicals have been chosen to cause an exothermic reaction when mixed. Interior membrane 250 that can be rendered permeable, separates the first and second chemicals in container 220. Internal membrane 250 can be rendered permeable through such actions as the application of physical force to container 220 while at the same time the impermeablity of outer membrane 110 is maintained.

Outer wrap 170, which covers at least the area to be placed on the user's face (see FIG. 7), is made of soft, non-abrasive, lint-free material 180 such as gauze. Material 180 is suitable for absorbing and retaining a cleansing substance suitable for cleansing the peri-orbital region. Material 180 is also suitable for absorbing and retaining a topical non-allergenic bacteriostatic or bactericidal antibiotic. Material 180 is also flexible in the region to be applied to the face so that the contained cleanser and/or antibiotic can be moved around the peri-orbital region to cleanse the region.

Arcuate handle 280, having finger slot 290 allows a user's fingers to wrap around and better hold arcuate handle 280. Arcuate handle 280 can penetrate into first adjacent storage area 230 with one arm 300, and into second adjacent storage area 240 with the other arm 310. Outer membrane 110 can be sealingly attached to the sides of arcuate handle 280, to maintain the impermeability of container 220. Alternatively, the arms of arcuate handle 280 can be attached to the exterior of outer membrane 110.

FIG. 7 shows the application of an eye pad, such as described herein, to peri-orbital region 320 of a user. Referring now to eye pad system 22, an impermeable outer membrane 110 is sized to fit generally within a user's peri-orbital region 320, and is sufficiently flexible to mold to the eye region of the user's face. Internal membrane 200 has been rendered permeable by rupture. First chemical 120 and second chemical 140 are mixed in the container defined by the impermeable outer membrane 110. The first and second chemicals have been chosen to cause an exothermic reaction when mixed, releasing heat 210 from the system 22. Impermeable outer membrane 110 remains impermeable when internal membrane 200 is rendered permeable.

Outer wrap 170, which covers the area to be placed on the user's face but does not cover the complete outer membrane 110, is made of soft, non-abrasive, lint-free material 180 such as gauze. Material 180 is suitable for absorbing and retaining a cleansing substance suitable for cleansing peri-orbital region 320. Material 180 is also suitable for absorbing and retaining a topical non-allergenic bacteriostatic or bactericidal antibiotic. Material 180 is also flexible in the region to be applied to the face so that the contained cleanser and/or antibiotic can be moved around peri-orbital region 320 to cleanse the region.

Arcuate handle 280 is attached to outer membrane 110 on the side of system 22 opposite that to be applied to the user's face. Arcuate handle 280 can aid in applying pressure to rupture an intact internal membrane 200, and can assist user in holding system 22 at or around peri-oribital region 320. To further aid the user in handling system 22, the portion of the container facing away from the facial-contact region, and to which arcuate handle 280 is affixed, can be firmer and less flexible than the facial-contact region.

Figure 8:
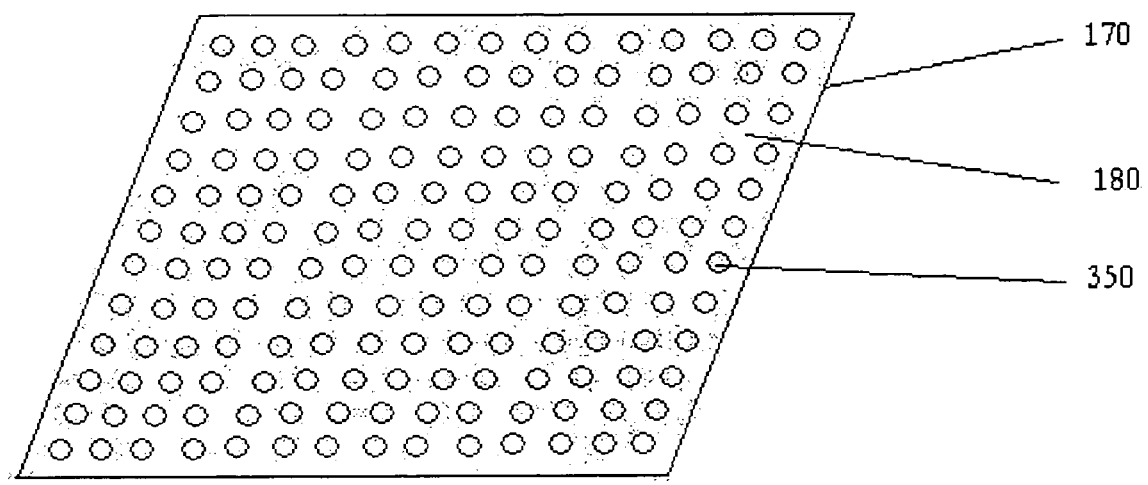
FIG. 8 shows a material that contains cleansing and/or antibiotic in breakable capsules.

FIG. 8 provides an example of an outer wrap 340. In this embodiment, small breakable capsules 350 are contained in material 180. Each capsule 350 holds cleansing material, antibiotic, or a combination thereof. Each capsule 350 can be broken, such as by the same application of pressure used to cause internal membrane 160 or 250 to be rendered permeable. Capsules 350 then release their contents into material 180, to be massaged onto the skin of the peri-orbital region 320. This embodiment is especially useful when the cleansing material and/or the antibiotic needs to be protected from the air in order to prolong its life.

Figure 9:
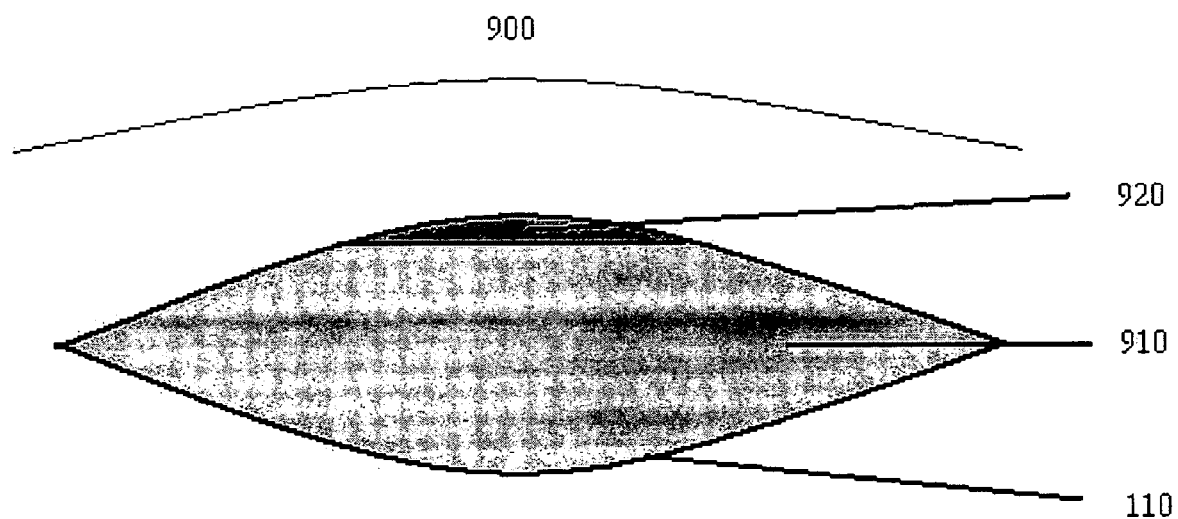
FIG. 9 shows a cross sectional view of an exothermic heat pack which utilizes the heat generated by the crystallization of an organic salt which initiates when a metal piece is bent inside a container.

FIG. 9 depicts a cross sectional view of an eye pad, compress pouch, or exothermic heat pack (container 900) which utilizes the heat generated by the crystallization of an organic salt (e.g., Sodium Acetate) 910. The salt may be liquid under ordinary conditions in room temperature, but freezes (i.e., crystallizes) rapidly when a metal piece (e.g., a stainless steel disk, rod, or other) (920) is bent inside the container, releasing steady-state heat as a byproduct. Bending the metal piece causes a molecular interaction with the chemical 910. The metal piece should have a shape and dimension that allow it to be easily bent by a person's fingers alone. A score line 930 may be added to make the piece easier to bend (see FIG. 10). The metal piece can be free floating or, as in the example shown in FIG. 9, attached to the wall of the container. The chemicals may be encased inside a non-permeable, non-breakable, preferably transparent outer membrane 110 (e.g., Vinyl).

Figure 10:
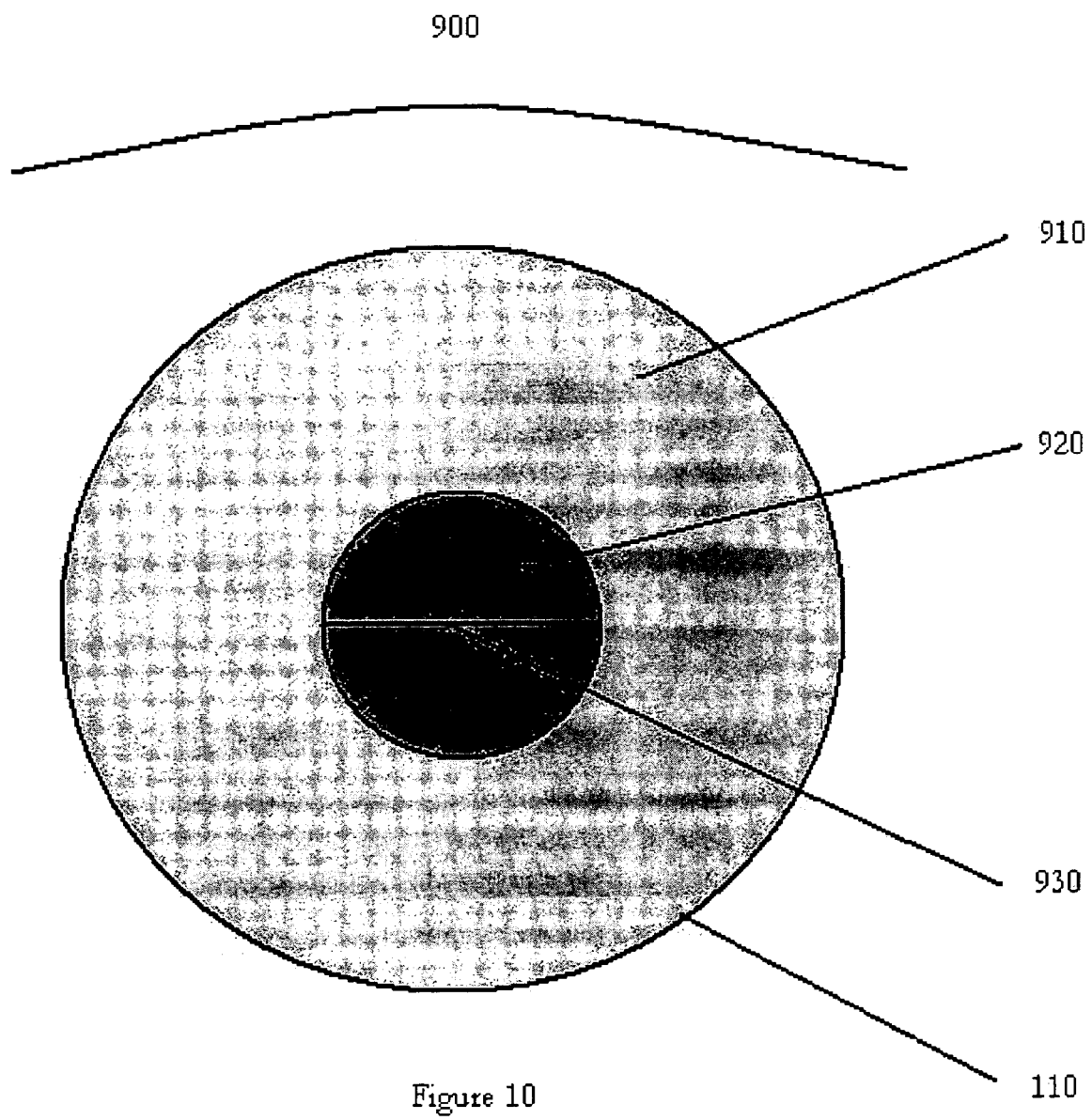
FIG. 10 depicts a top view of the exothermic heat pack of FIG. 9.

FIG. 10 depicts a top view of the container 900.

Figure 11:
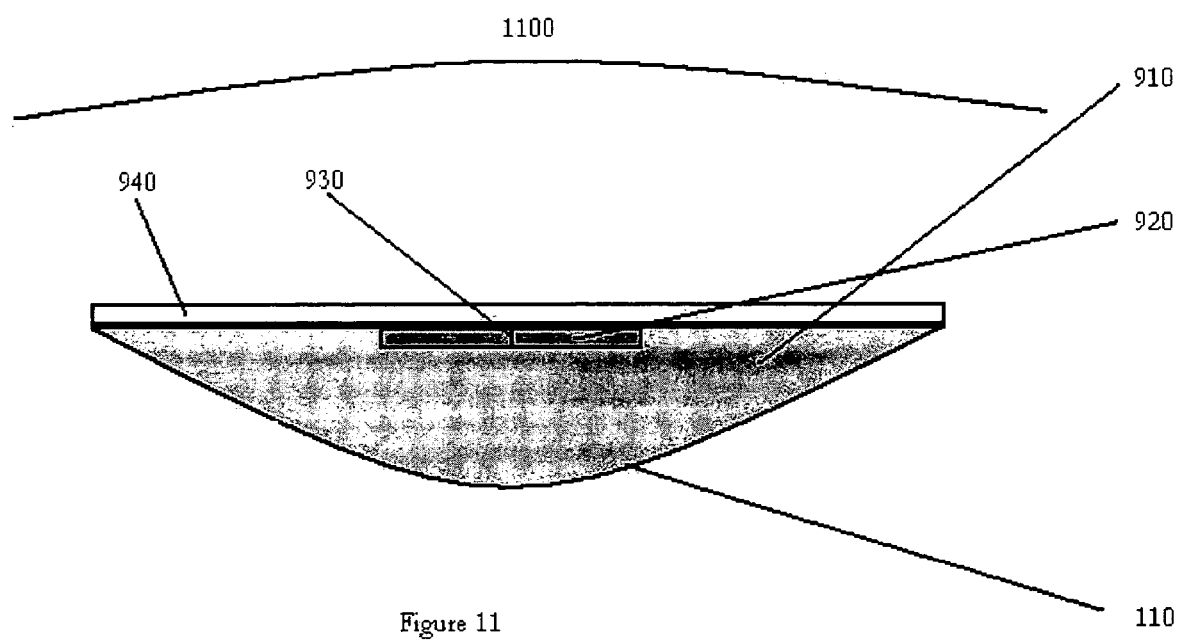
FIG. 11 depicts a cross section view of an exothermic heat pack with an added handle attached to the outside of an outer wall, with the metal piece attached to the inside of the wall placed under and in the center of the handle.

FIG. 11 depicts another embodiment of the invention, as container 1100, which may have the same specifications as container 900 in FIGS. 9 and 10, with an added handle (940) attached (e.g., glued) to preferably the center of the outer wall (110) as shown, at one end of the container, with the metal piece (920) attached to the center of the inner wall placed under the handle. The handle is preferably made of a hard plastic that can be easily bent by a person. When this handle is bent in half (by a person's fingers alone), it will bend with it the metal piece inside the container and initiate the exothermic reaction. At the same time, this handle may protect the fingers from the heat generated by the exothermic device.

Figure 12:
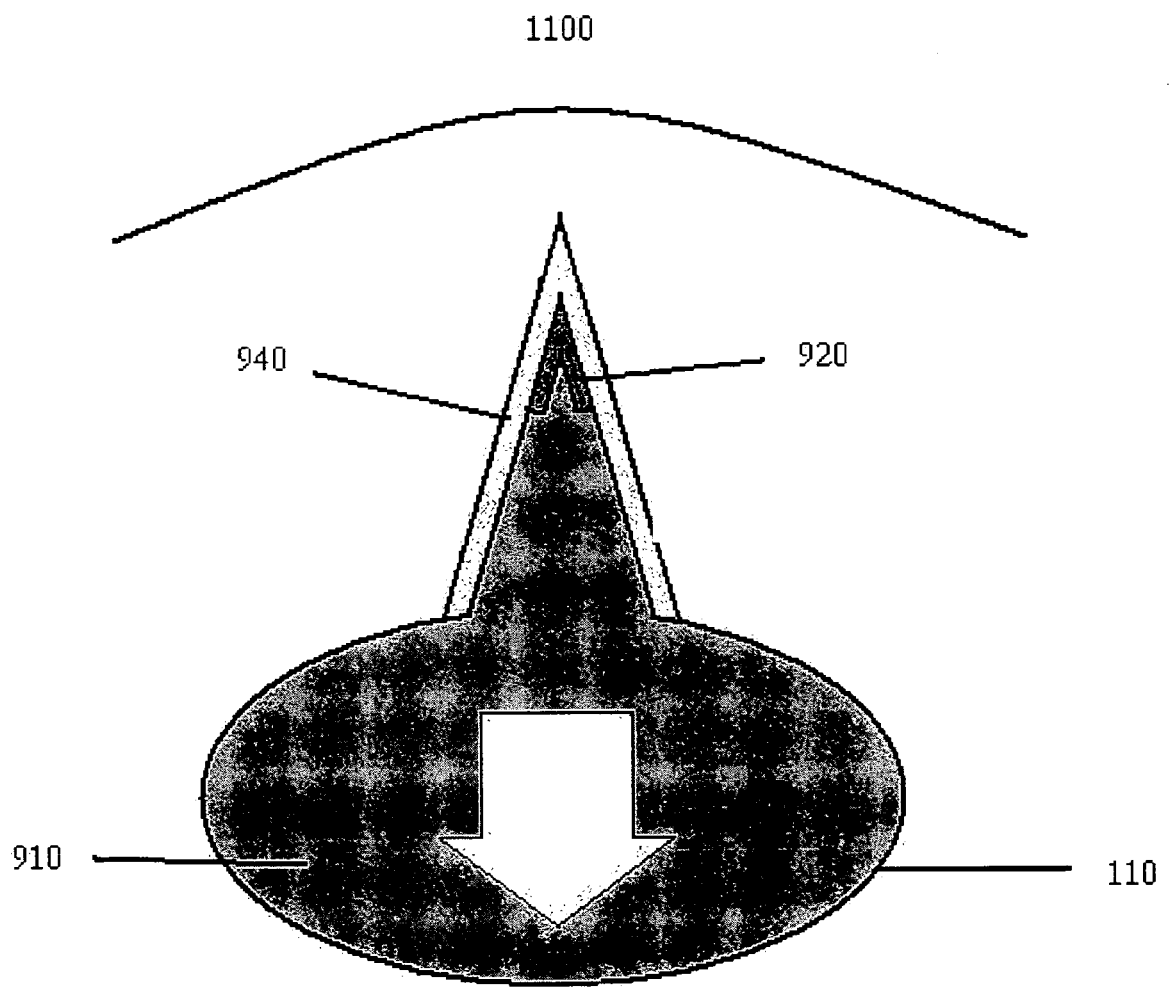
FIG. 12 depicts the heat pack with its handle bent, and the metal piece bent inside the container.

FIG. 12 depicts the heat pack with its handle bent in half. Note how this creates pressure that causes a ballooning of the outer wall of the container (at the opposite end), pushing the liquid chemical (e.g., Sodium Acetate) in a forward direction (indicated by the arrow in FIG. 12).

Figure 13:
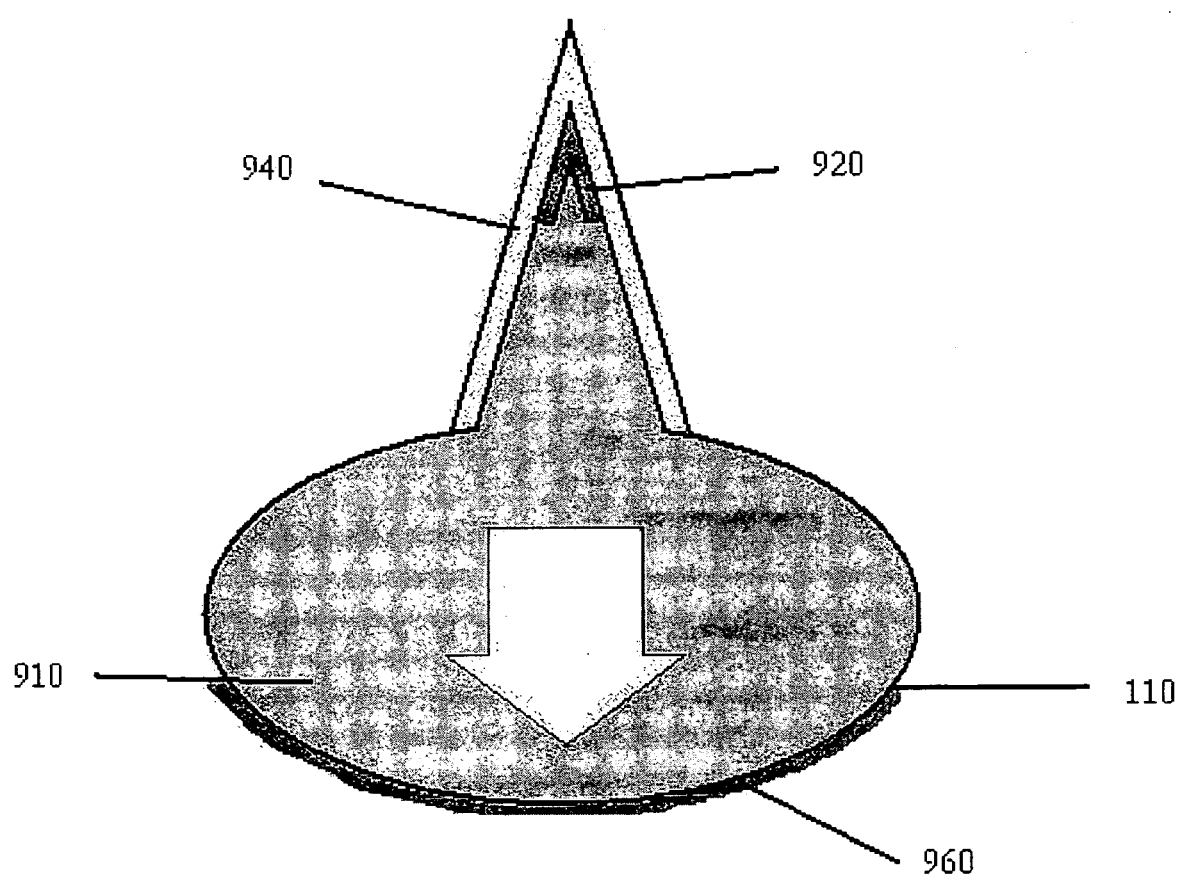
FIG. 13 depicts the heat pack of FIG. 12 with an added pad preferably made of non-abrasive, lint-free material (e.g., gauze) attached to the outside of the container, opposite the handle.

FIG. 13 depicts the heat pack of FIG. 12 with an added pad 960, preferably made of a non-abrasive, lint-free material (e.g., gauze). The material is preferably glued to the outside surface of the outer wall 110, opposite the handle. The material 960 may stop short of covering the entire surface of the outer wall, as shown in the example of FIG. 13, allowing a view of the crystals inside the container through a preferably transparent outer wall. As an alternative, the material 960 may be wrapped around the entire surface of the outer wall 110 (in the case where no handle 940 is provided). This material may be pre-soaked in a hypoallergenic, antibacterial, pH-controlled detergent (e.g., baby shampoo), with or without an antibiotic formulation (e.g., erythromycin, bacitracin, or neomycin/polymyxin).

Figure 14:
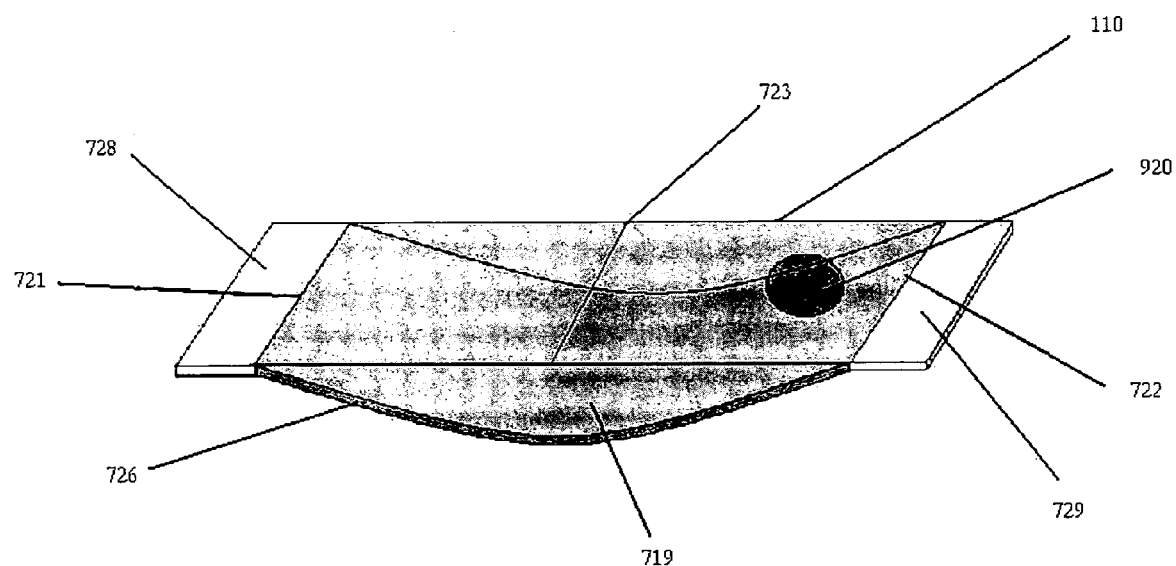
FIG. 14 depicts a 3-dimensional view of an alternate design for the exothermic warm compress.
Figure 15:
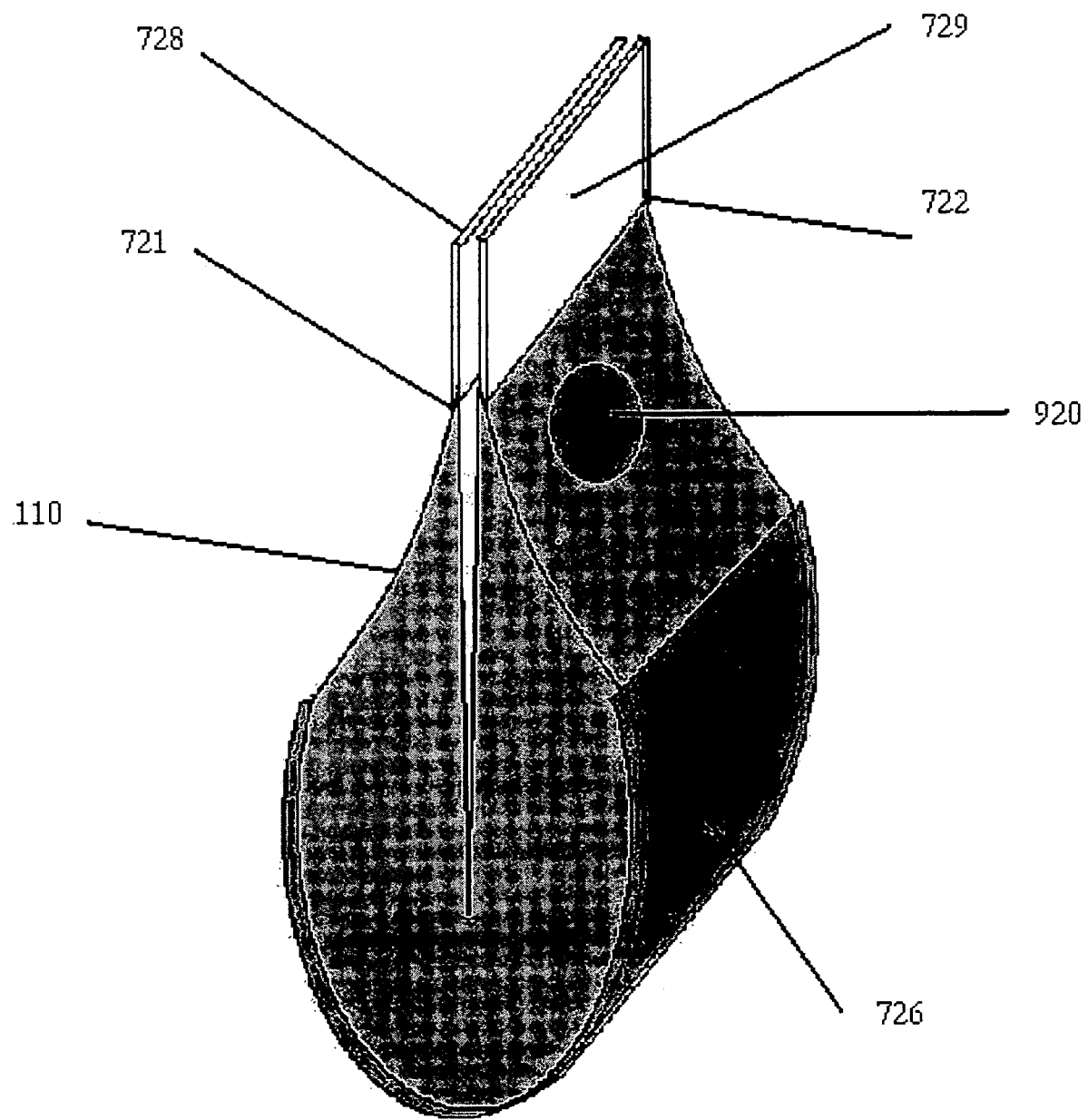
FIG. 15 depicts a 3-dimensional view of the example compress in FIG. 14 when bent.
Figure 17:
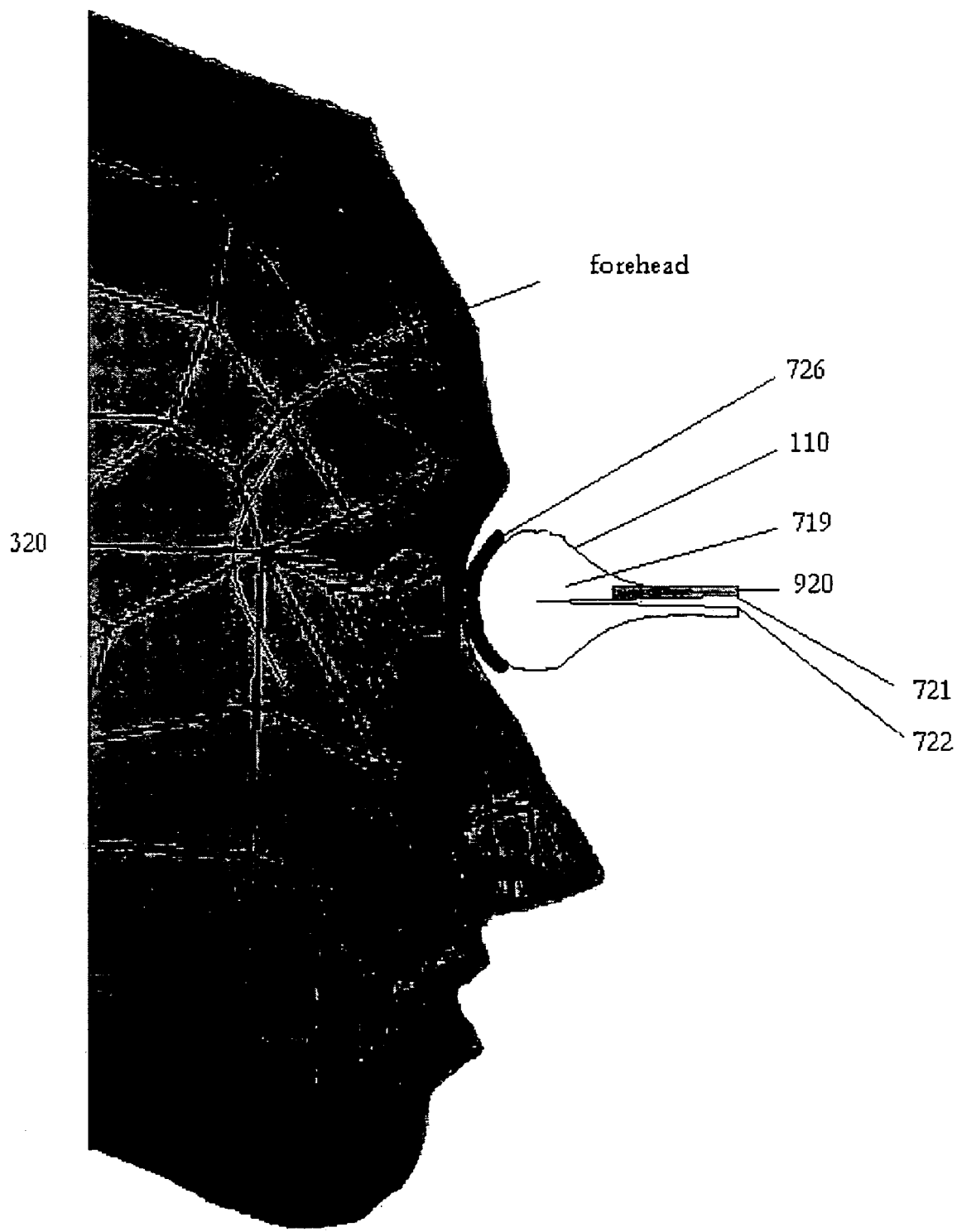
FIG. 17 depicts a warm compress similar to that in FIG. 15 when applied to the periorbital area. The extension of the outer impermeable membrane may be used as a handle to hold and maneuver this product.

FIG. 14 depicts a 3-dimensional view of an alternate design for the exothermic warm compress. In this figure the compress is depicted in its flat configuration. Here, the metal piece 920 can be free-floating inside, or it can be attached to an inside wall (also referred to as inner wall) of the outer non-permeable membrane 110, and is in contact with another chemical 719 inside the closed bag that is formed by the outer membrane 110. The edges or ends 721, 722 of the non-permeable outer membrane 110, when moved towards each other as a portion 723 of the membrane 110 between them is bent, will serve as a handle that can be used to grab the compress between the thumb and the forefinger and/or middle finger of the user's hand (see FIG. 15, which shows the compress folded in half, and the metal piece 920 bent as a result). A piece 726 of absorptive material, presoaked in a pH-controlled detergent, with or without an ophthalmic antibiotic solution, may be attached to the central part of the outer non-permeable membrane 110 (centered between the two ends 721, 722), on its outside, as shown. This material will thus be in direct contact with the periocular skin when the compress is in use. FIG. 17 shows an instance of use of the embodiment of FIG. 14, where the far end of the folded compress is pressed against the user's peri-orbital region 320, and its near ends 721, 722 can be grasped by the user's hand (not shown). Note that handle extensions 728, 729 can be provided that extend beyond the ends 721, 722, as shown in FIG. 14.

In a preferred embodiment, the invention provides a one step treatment of a variety of conditions of the eyelid region. Instead of relying on the separate elements of heat, detergent and antibiotic, all two (or three if an antibiotic is needed) may be joined into one device, designed to:

1) provide steady-state heat at a safe maximum temperature (controlled by the thermodynamic nature of the reaction)
2) provide heat for an acceptable period of time for this heat to be effective
3) mold to the external surface of the eyes (over the eyelids) as to treat a desired surface area
4) allow for simultaneous application of a safe, pH-controlled, detergent to the eyelid margins, lashes and the meibomian orifices
5) provide a non-abrasive, lint free cloth which will be presoaked with the detergent and can be used to safely massage the delicate eyelid skin
6) provide a convenient handle which facilitates holding and maneuvering the compress, thereby making massaging the eyelids and lashes much more convenient
7) provide a handle which protects the fingers from burning and contaminating the sterile pad which will come in contact with the eyes.

It is thought that in treating the aforementioned conditions, the provided heat causes the clogged meibomian gland orifices (which drain behind the insertions of the eyelashes at the eyelid margin) to widen. This allows the viscous meibomian discharge to drain more easily, while drawing detergent and antibiotic into the openings of these orifices.

This exercise improves the viscosity of the oily meibomian discharge, destroys the abnormal microbacterial flora that has lead to the overall poor hygiene of these orifices, and ultimately relieves the blockage.

Performed separately, the lid scrubs are not as effective as without the heat, the gland orifices are clogged and narrowed due to the residing abnormal bacterial flora and the resulting inflammation, and the detergent and antibiotic molecules do not penetrate as easily.

A preferred embodiment of the invention is comprised of a heat source, which utilizes an exothermic chemical reaction, supplied in a small, flexible container to be applied over the eyelids. This source of heat energy can come from a number of variety of different chemical reactions which release heat as an enthalpic byproduct. The portion of the eye pad or compress that is in contact with the user's skin (e.g., when ready to contact the skin after folding the compress) may be no larger in area than that of the peri-orbital region of an eye (between the superior and inferior orbital rims, an the medial and lateral walls of the human's orbit). Each pad may be individually packaged in a sterile container.

Figure 16:
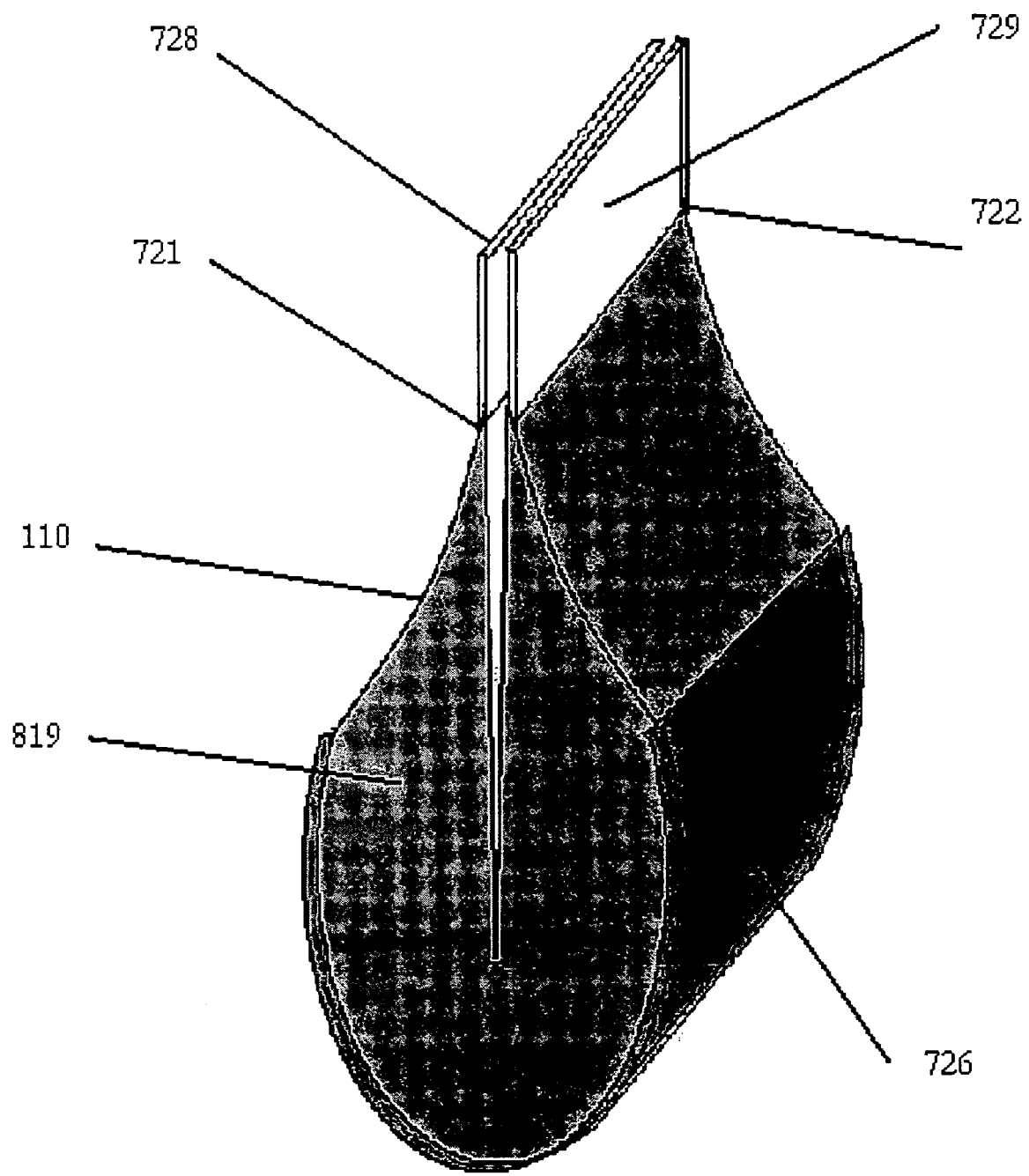
FIG. 16 depicts a 3-dimensional view of a non-exothermic warm compress similar in structure to that in FIG. 14, except that the chemical with which it is filled is composed of a reheatable material (e.g., glycerin gel), and no metal piece 920 is provided.

Such exothermic processes include, but are not limited to reactions that generate heat either when two different ingredients or chemicals are intermixed (e.g., Magnesium Sulfate and Water), or when a metal piece (e.g., stainless steel disk) is physically altered (bent) inside a container filled with a liquid organic salt (e.g., Sodium Acetate), or when a metallic powder (e.g., Iron dust) is exposed to the air using a catalyst to expedite the oxygenation (rusting) of iron. In addition, a reheatable liquid or solid chemical (by boil or microwave) (e.g., glycerin) held inside the impermeable container may also serve as a heat source for this application. In the latter scenario, no exothermic reaction inside the container is required. See, for example, the embodiment depicted in FIG. 16 which has a structure similar to that of FIGS. 14-15, except that the chemical 719 has been replaced with a reheatable chemical 819 and no metal piece 920.

In one embodiment, a small outer container is made of an air-tight bag or other flexible container, for example made from plastic, vinyl or silicone. The first container is filled with one of the two ingredients of an exothermic chemical reaction (e.g., Magnesium Sulfate). Inside this outer container, there is another smaller, tightly-sealed, breakable sack or balloon, which contains the second ingredient (e.g., water) (FIG. 1). This pack includes or may be wrapped with a soft material that is preferably lint-free and/or non-abrasive (e.g., gauze or other woven absorption material, lint-free cotton or other such absorptive material), which has been or is then pre-soaked in a mild, pH-controlled, and preferably hypoallergenic (thereby non-irritating) antibacterial detergent, with or without a topical ophthalmic antibiotic solution (pre-soaked and sold in the sterile container). Before use, the consumer applies pressure to the inner bag (through the outer container) causing it to break, thereby mixing the two necessary ingredients and initiating the exothermic reaction. (FIG. 2).

In another embodiment, the warm compress is made of an air-tight bag or other flexible, air tight container, for example made from plastic, vinyl or silicone. The container has been filled with a liquid chemical (e.g., Sodium Acetate), and contains a metal piece inside the solution (e.g., a stainless steel disk or plate). Before use, the consumer applies enough pressure to the metallic piece through the outer wall to bend it, thereby initiating a rapid exothermic crystallization process.

The heat pack is then massaged over the eyelids for the duration of the exothermic phase of the reaction. The temperature of the heat source is controlled and remains approximately the same for a desired period of time. The surface of the covering material that comes in contact with the skin includes a gentle detergent with or without an ophthalmic antibiotic solution. This solution or combination of solutions can be present on the surface when the product is unwrapped, or one or more containers of the solution(s) can be provided, into which the unwrapped heat pack is dipped prior to use.

The combination of these elements is a flexible product for placement on the periocular region for treating or preventing a variety of the aforementioned conditions that commonly affect the eyelids.

Uses

This product may be utilized in any of the conditions of the eyelids aforementioned, in which the use of heat has been indicated by the American Academy of Ophthalmology, the National Eye Institute, and/or any of the major comprehensive texts of Ophthalmology. The etiology may be infectious (e.g., blepharitis, meibomitis, acute dacryocystitis, orbital or preseptal cellulitis); inflammatory (e.g., inflamed hordeola, chalazia, or contact dermatitis), or combinations thereof. Additionally, dry-eyes, conjunctivitis/keratitis as caused by wearing contact lenses, can be treated in this manner.

Ophthalmic infection (endophthalmitis) is a feared complication of any ocular operation (e.g., cataract extraction, corneal transplantation, refractive surgery (e.g., LASIK), glaucoma and retinal surgery). Intra-operative contamination of the surgical field with the bacteria that usually reside on the eyelashes and the eyelid margins has been found to be a major nidus for infection. As a result, proper eyelid hygiene has become a prerequisite to any intraocular procedure, and a gold standard of ophthalmic surgery today. An embodiment of the invention lies in using the heat pack to improve eyelid hygiene prior to eye surgery, and may help reduce the possibility of complications that may arise from operating on an eye with existing, poor hygiene or poorly-treated blepharitis.

The heat pack is also useful following any intra- or extraocular surgery to provide for symptomatic relief as well as to provide a clean sterile environment until the fresh wounds re-epithelialize, further reducing any chance of infection.

Eyelid edema and/or hematomas resulting from orbital contusion injuries are also thought to resolve faster with the use of the invention's warm compress (e.g., after an initial 48-hour period of using ice to minimize the initial phase of the inflammatory response).

Heat Source

The heat source is provided by a small, flexible container as described above. Both temperature and duration of the heat production are controlled so as to provide sufficient heat without damaging tissue. For instance, the maximum temperature reached should not be so high as to burn the skin. The temperature and length of time of the reaction can be controlled by the choice of chemicals used to create the reaction, and by the amount of the chemical prior to mixing. In one embodiment of the invention, the preferred temperature is as high as 55° C., in view of the amount of heat that can be transferred to the skin through e.g. a thick pledget or cloth attached to the outside surface of the container.

In a preferred embodiment, the compounds used to create the exothermic reaction are inert and/or not irritating to skin so that no injury occurs in case the impermeable outer wall breaks and releases the compounds. The compounds should also be environmentally friendly so that the products can be easily and safely disposed of after use.

In one embodiment, the heat source maybe reusable, and the only thing that will be replaced in each use is a pre-moistened cloth or other absorptive material that may wrapped on the outside of the container. An example would be one which utilizes the crystallization phenomenon between sodium acetate and stainless steel. After the liquid freezes (crystallizes) and the heat has been released, the solid (crystal) phase of the chemical may be returned to liquid form, by heating it (e.g., either bringing the pack to a boil or heating it up in a microwave oven. After the product cools, the chemical will stay in liquid form, and by disturbing the metal piece, the crystallization process starts yet again.

With respect to the embodiment in which the reheatable eye pad is filled with a chemical such as glycerin gel, the eye pad is first heated (e.g., by being placed in hot or boiling water, or by being heated in a microwave oven) in accordance with specific instructions. Thereafter, once it reaches the appropriate temperature range, the eye pad is placed in contact with the periocular region and eyelid, and pressed and/or moved around the region to massage the eyelid.

Structure

In one preferred embodiment, one pouch is contained inside of the second pouch, as is shown in FIGS. 1-3. Although these figures show the eye pad as spherical, it can take any shape as long as it is flexible enough to mold to the approximate shape of the user's periorbital region.

In the example shown in FIGS. 1-3, one of the substances is a liquid while the other is a powder, although other forms are acceptable. When the membrane between these compounds is broken, the two ingredients intermix to initiate the exothermic reaction and release adequate heat energy to rapidly raise the temperature of the eye pad to the desired level, and to maintain the reaction for the desired period of time or longer.

In another preferred embodiment, the pouches abut each other, as shown in FIG. 4. Examples of the breakable membrane include but are not limited to plastics, silicone and combinations thereof.

In another preferred embodiment, the ingredients of the reaction may be contained within the same container (e.g., liquid salt and a metal disk). Once the metal disk is physically altered (bent), it initiates a crystallization reaction which releases heat as a byproduct.

Chemical Reaction

Examples of combinations that will work in the described embodiments to create exothermic reactions include water plus magnesium sulfate, and liquid sodium acetate trihydrate plus stainless steel. Other combinations that result in the appropriate temperature and that have reactions that maintain the temperature for the desired period of time, or are reheatable by boiling or microwaving (e.g., glycerin gel) are also included.

Shape

The heat pack or pouch is sufficiently flexible to fit within the user's peri-orbital region, with little or no overlap to the rest of the face. This allows application of heat to the desired area without overlapping onto areas that do not need the treatment. Further, it allows the pouch to be more flexible, and more easily handled.

Handle

A handle, such as one made of the same material as the pouch's outer wall or membrane (e.g., vinyl/silicone), or alternatively, of a lightweight but sturdy plastic, can be used as part of the eye pad. The handle is placed away from the portion of the eye pad that will contact skin. Preferably it is placed away from any cleansing material. The handle can be of any shape or construction that enables the user to easily hold the eye pad in place for the prescribed period of time. Examples are shown in FIGS. 4, 11, 12, and 13.

The pouches are preferably disposable. They can be made of lightweight low-cost materials that need not withstand long periods of use, and are therefore inexpensive and easy to handle for the user, e.g., an outer wall made of Vinyl.

Cleansing Material

In addition to the heat source, the pouch may contain a cleansing material to clean the periocular region. The material in that case would be on the outside of the pouch so as to be next to the skin. The heat pack may be wrapped in a soft, non-abrasive, lint-free material (e.g., cotton or rayon pledgettes or cloth); may have a section of such material attached to it on the side that will be in direct contact with the skin; may be composed of such material; or may have the material provided in any other manner that will allow the material to contact the peri-orbital skin.

In a preferred embodiment, a cleansing substance that is gentle to the skin yet thoroughly cleanses the area is present in the material. Alternatively, a container of such a solution can be supplied with the pouch, to be applied to the material prior to placing the pouch on the skin. In yet another embodiment, the cleanser can be packaged within the material, for example using small breakable cells containing the cleanser, and released by pressure such as is used to initiate the exothermic reaction.

Cleansing Solution

Cleansers can include, but are not limited to any detergent that has been pH controlled not to cause any ocular irritation or cause harm to the cornea if it gets into the eye, and is preferably hypoallergenic. One preferred example is a pH-controlled "baby" shampoo. Preferably the cleanser has antibacterial qualities that can improve the removal of bacterial flora from the treatment area.

Antibiotic

In another preferred embodiment, a topical ophthalmic bacteriostatic or bactericidal antibiotic is also present. As with the cleanser, the antibiotic can be supplied in or on the material or packaged within the material. Alternatively, it can be supplied separately, alone or mixed with the cleanser, to be applied to the material prior to placement of the pouch on the skin.

Any antibiotic that can reduce the number of bacterial colonies residing in the peri-ocular adnexa can be used. Antibiotic solutions can include, but are not limited to, Bacitracin, Erythromycin, Gentamicin, Polymyxin or Neomycin. Bacitracin and Erythromycin ophthalmic ointments are preferred because they have a wide spectrum of activity and are usually very well tolerated, and are the most commonly prescribed antibiotics to treat Blepharitis today. Topical fluoroquinolones, including, but not limited to, Ciprofloxacin, Norfloxacin, Ofloxacin, and Moxifloxacin may also be utilized in this product as these formulations have very broad antibiotic coverage, pose minimum chances of bacterial resistance, and are very well tolerated by patients.

Method of Use

In a preferred embodiment, the product is a small, flexible eye pad that can fit within the peri-orbital region without substantially overlapping other skin. It may have a sterile wrapping. The user preferably cleans his/her hands before unwrapping the eye pad. Prior to use, and preferably while the eye pad is still wrapped, the user massages the container to mix the detergent, with or without antibiotic, mixture and "foam" the non-abrasive material that surrounds the heat pack. S/he then breaks the barrier between the two compartments by applying digital pressure, starting the exothermic reaction. Alternatively, the user may open the wrap and bend a plastic handle that, in turn, bends a metallic disk inside the container, initiating the exothermic reaction. Alternatively, the user may heat the pack inside a microwave, and then apply a non-abrasive material, presoaked with the detergent over it before massaging the eyelids.

If the cleanser and/or antibiotic are also contained in breakable compartments, this action will also release these components into the non-abrasive material on the eye pad. (If the cleanser and/or antibiotic are provided separately from the heat pack, the cleanser and/or antibiotic are applied to the material after removing the wrapper.)

If the compress is manufactured as a reusable heat source, the user will boil or microwave the pack, let it cool, and apply a premoistened pledget or cloth to one surface of the pad, then bend the handle to initiate the reaction; the cloth will be thrown away after use.

The user holds the compress by its handle (if provided), and gently massages the side of the eye pad having the cleanser and antibiotic around the affected peri-orbital region for a period of about 5-15 minutes as tolerated. After use, the warm pad and/or the cloth are discarded.

EXAMPLES

The following examples illustrate some embodiments of the invention.

Example 1

As depicted in FIG. 13, a soft transparent vinyl bag, about 2 inches in diameter and ½ inch in thickness is obtained from, for example, Emori Development Ltd. which is filled with Sodium Acetate. A small, thin metal disk about ½ inch in diameter, and ½ mm in thickness, is attached (e.g., glued) to the top center of the inner wall, or left free floating inside the bag. A sturdy round plastic handle about one inch in diameter and 1-2 mm in thickness is heat-pressed to the top center of the outer wall. A 1-2 mm thick non-woven (cotton/rayon) pledget or a soft, lint-free, non-abrasive cloth is attached to the bottom of the pack (opposite the side of the handle), which is pre-moistened with a baby shampoo formulation obtained from, for example, Neutrogena, Inc. The pledget may also include a dilute mixture of Erythromycin or Bacitracin Ophthalmic Antibiotic formulation obtained from, for example E. Fougera & Co. Melville, N.Y.). The eye pad is wrapped under sterile conditions in a plasticized paper covering which prevents the moistened pad from drying, keeps the compress sterile, and is easily removable by the user. The warm compress may be applied over the closed eye(s) by the user, grabbed by its handle, over the entire eyelid margin to scrub the eyelashes, or over an area of the eyelid affected by, for example, a stye.

Example 2

A 2 inch by 2 inch by 3 inch flexible heat pack is obtained from, for example, Hospital Marketing Services (HMS) Co, Inc. The heat pack has two compartments, one containing magnesium sulfate in powder form, and the other containing water in an inner breakable plastic balloon. A round hard plastic handle is attached to the pack on one end. The heat pack is covered with a soft, lint free material, such as a layer of polyester and several layers of gauze. The gauze surrounding the heat pack is coated with a mixture of a pH-controlled shampoo (Johnson & Johnson or Neutrogena) with or without Bacitricin Ophthalmic Ointment (E. Fougera & Co. Melville, N.Y.) or Ciloxan Ophthalmic Solution (Alcon, Inc.) in an amount sufficient to transfer to the user's skin when the eye pad is being used. A removable piece of plastic is optionally placed over the coating to keep the coating in place. The eye pad is wrapped under sterile conditions in a plasticized paper covering which is easily removable by the user.

Example 3

Use of Product to Treat Chalazia

A patient presenting with a chalazion (stye) is advised to start using this product immediately after the onset of symptoms, and to follow up with his/her ophthalmologist as soon as possible. The patient foams the pack inside its sterile wrap and breaks the inner container by applying force. The patient then unwraps the heat pack, holds it by its handle. The patient then gently places the eye pad against the affected eyelid and moves the eye pad in small circles across the skin for five to ten minutes. When the treatment is finished, the patient disposes of the eye pad in the trash.

What is claimed is:

1. A compress for treating eye conditions comprising:
   a sealed container having an impermeable outer membrane and being sized to fit generally within the peri-orbital region, the container being sufficiently flexible to mold to the shape of the eye, the membrane being impermeable to a chemical within the sealed container; and
   a metal piece inside the sealed container and in contact with the chemical, the chemical to crystallize when the metal piece is physically altered thereby releasing heat as a byproduct.

2. The compress of claim 1 further comprising a piece of absorptive material to absorb an amount of a cleansing substance that does not cause corneal irritation if it comes in contact with the eye, the piece of absorptive material being attached to an outside surface of the container and sized to allow the container, despite the attached piece of absorptive material, to still fit within the peri-orbital region.

3. The compress of claim 2 further comprising a single, sterile package inside which the container, the piece of absorptive material, and the absorbed amount of the cleansing substance are sealed.

4. The compress of claim 2 further comprising an amount of an ophthalmic antibiotic solution retained in the absorptive material.

5. The compress of claim 2 further comprising a handle, attached to the outside surface of the container.

6. The compress of claim 5 wherein the handle is attached at a position that is aligned with the metal piece, and is rigid enough, so that bending the handle also bends the metal piece simultaneously.

7. A compress for treating eye conditions, comprising:
   a sealed container having an impermeable outer membrane and being sized to fit generally within the peri-orbital region, the container being sufficiently flexible to mold to the shape of the eye, the outer membrane being impermeable to first and second chemicals within the sealed container that are selected to have an exothermic reaction when mixed,
   the container having an inner membrane that is to separate the first and second chemicals but rupture when force is applied to the container thereby allowing the first and second chemicals to mix,
   the outer membrane to remain impermeable to the first and second chemicals while said force is applied and after the first and second chemicals have mixed.

8. The compress of claim 7 further comprising a piece of absorptive material to absorb an amount of a cleansing substance that does not cause corneal irritation if it comes in contact with the eye, the piece of absorptive material being attached to an outside surface of the container and sized to allow the container, despite the attached piece of absorptive material, to still fit within the peri-orbital region.

9. The compress of claim 8 further comprising a single, sterile package inside which the container, the piece of absorptive material, and the absorbed amount of the cleansing substance are sealed.

10. The compress of claim 7 further comprising an amount of an ophthalmic antibiotic solution retained in the absorptive material.

11. The compress of claim 7 further comprising a handle, attached to the outside surface of the container.

12. A compress for treating eye conditions comprising:
a sealed container having an impermeable outer membrane enclosing an interior volume of the container, the container being sized to fit generally within the peri-orbital region and sufficiently flexible to mold to the shape of the eye, a heat source disposed within the interior volume of the container to release heat via an exothermic reaction;
a piece of absorptive material attached to the outer surface of the impermeable outer membrane, said piece of material being capable of retaining therein an amount of cleansing substance suitable for use on the eye or an amount of ophthalmic antibiotic solution; and
a handle attached to the container.

13. The compress of claim 12 wherein the heat source comprises a liquid and a metal piece, the liquid to crystallize when the metal piece is physically altered thereby releasing heat via the exothermic reaction.

14. The compress of claim 12 further comprising said amount of cleansing substance retained in the piece of absorptive material.

15. The compress of claim 14 further comprising a sealed, sterile package in which the container, together with the attached handle, the piece of absorptive material and the retained amount of cleansing substance, are contained.

16. The compress of claim 12 further comprising said amount of ophthalmic antibiotic solution retained in the piece of absorptive material.

17. The compress of claim 16 further comprising a sealed, sterile package in which the container, together with the attached handle, the piece of absorptive material and the retained amount of ophthalmic antibiotic substance, are contained.

18. The compress of claim 12 wherein the piece of material is located away from the handle.

19. The compress of claim 18 further comprising said amount of cleansing substance retained in the piece of absorptive material.

20. The compress of claim 19 further comprising a sealed, sterile package in which the container, together with the attached handle, the piece of absorptive material and the retained amount of cleansing substance, are contained.

21. The compress of claim 18 further comprising said amount of ophthalmic antibiotic solution retained in the piece absorptive material.

22. The compress of claim 21 further comprising a sealed, sterile package in which the container, together with the attached handle, the piece of absorptive material and the retained amount of ophthalmic antibiotic substance, are contained.

23. The compress of claim 12 further comprising said amount of cleansing substance and said amount of ophthalmic antibiotic solution, both retained in the piece of absorptive material.

* * * * *